(12) United States Patent
Barstad

(10) Patent No.: US 6,576,438 B2
(45) Date of Patent: Jun. 10, 2003

(54) METHOD OF DETERMINING THIOPURINE METHYLTRANSFERASE ACTIVITY

(75) Inventor: Paul Barstad, Hamilton, MT (US)

(73) Assignee: Prometheus Laboratories, Inc., San Diego, CA (US)

( * ) Notice: Subject to any disclaimer, the term of this patent is extended or adjusted under 35 U.S.C. 154(b) by 141 days.

(21) Appl. No.: 09/859,819

(22) Filed: May 16, 2001

(65) Prior Publication Data

US 2002/0028476 A1 Mar. 7, 2002

Related U.S. Application Data

(60) Provisional application No. 60/205,695, filed on May 19, 2000.

(51) Int. Cl.$^7$ ................................................ C12Q 1/48
(52) U.S. Cl. ........................................................ 435/15
(58) Field of Search ........................................... 435/15

(56) References Cited

PUBLICATIONS

Breithaupt et al., "Quantitative high pressure liquid chromatography of 6–thioguanine in biological fluids," *J. Chromatogr. Sci.* 19:496–499 (1981).
Burchenal et al., "Clinical Evaluation of a New Antimetabolite, 6–Mercaptopurine in the treatment of leukemia and allied diseases," *Blood* 8:965–999 (1953).
Boulieu et al., "Methylated and Non Methylated Thiopurine Nucleotide Ratio (ME6–MPN/6–TGN) : Usefulness in the Monitoring of Azathiopurine Therapy?" *Purine and Pyrimidine Metabolism in Man X*, 361–367 (Kluwer Academic/Plenum Publishers 2000).
Capdeville et al., "Interactions between 6–mercaptopurine therapy and thiopurine–methyl–transferase (TPMT) activity," *Eur. J. Clin. Pharmacol.* 46:385–6 (1994).
Dervieux and Boulieu, "Simultaneous determination of 6–thioguanine and methyl 6–mercaptopurine nucleotides of azathioprine in red blood cells by HLPC," *Clinical Chemistry* 44:551–555 (1998).
Dubinsky et al., "Pharmacogenomics and metabolite measurement for 6–mercaptopurine therapy in inflammatory bowel disease," *Gastoenterology* 118:705–13 (2000).
Ganiere–Monteil et al., "Thiopurine methyl transferase activity: new extraction conditions for high–performance liquid chromatographic assay" *J Chromatograph B.* 727:235–9 (1999).
Jacqz–Aigrain et al., "Thiopurine methyltransferase activity in a French population: h.p.l.c. assay conditions and effects of drugs and inhibitors," *Br. J Clin. Pharmacol.* 38:1–8 (1994).
Keuzenkamp–Jansen et al., "Thiopurine methyltransferase: a review and a clinical pilot study," *J Chromatogr B Biomed Appl.* 678:15–22 (1996).
Kirschner, "Safety of azathioprine and 6–mercaptopurine in pediatric patients with inflammatory bowl disease," *Gastroenterology* 115:813–821 (1998).

Kröplin et al., "Inhibition of thiopurine S–methyltransferase activity by impurities in commercially available substrates: a factor for differing results of TPMT measurements," *Eur. J. Clin. Pharmacol.* 55:285–91 (1999).
Kroöplin et al., "Thiopurine S–methyltranferase activity in human erythrocytes: A new HPLC method using 6–thioguanine as substrate," *Eur. J. Clin. Pharmacol.* 54:265–71 (1998).
Kröplin et al., "Determination of thiopurine methyltransferase activity in erythrocytes using 6–thioguanine as the substrate," *Adv. Exp. Med. Biol.* 431:741–5 (1998).
Krynetski et al., "Methylation of Mercaptopurine, Thioguanine, and Their Nucleotide Metabolites by Heterologously Expressed Human Thiopurine S–Methyltransferase," *Mol Pharmacol.* 47:1141–7 (1995).
Lennard and Singleton, "High–performance liquid chromatographic assay of human red blood cell thiopurine methyltransferase activity," *J Chromatograpy B.* 661:25–33 (1994).
Lennard, "The clinical pharmacology of the 6–mercaptopurine," *Eur. J. Clin. Pharmacol.* 43:329–39 (1992).
Mawatari et al., "Reversed–phase high–performance liquid chromatographic assay method for quantitating 6–mercaptopurine and its methylated and non–methylated metabolites in a single sample," *J Chromatograpy B.* 716:392–6 (1998).
McLeod, H.L., "Commentary on interactions between 6–mercaptopurine therapy and Thiopurine–methyl–transferase (TPMT) activity," *Eur. J Clin. Pharmacol.* 48:85–86 (1995).
Medard et al., "Thiopurine methyltransferase activity: new high–performance liquid chromatograpic assay conditions," *J Chromatograpy B.* 700:275–7 (1997).
Present et al., "6–Mercaptopurine in the management of inflammatory bowel disease: short–and long toxicity," *Ann. Intern. Med.* 111:641–9 (1989).

*Primary Examiner*—Sandra E. Saucier
(74) *Attorney, Agent, or Firm*—McDermott, Will & Emery

(57) ABSTRACT

The present invention provides a method of determining thiopurine methyltransferase (TPMT) activity in a subject. The method includes the steps of reacting sample obtained from the subject with a thiopurine derivative that is not 6-mercaptopurine to produce a methylated purine product; contacting the reacted sample with acid, thereby precipitating proteinaceous material from the reacted sample; separating supernatant from the precipitated proteinaceous material; and detecting in the supernatant the methylated purine product, where the amount of the methylated purine product indicates a level of thiopurine methyltransferase activity in the subject. In a method of the invention, the subject can be, for example, an inflammatory bowel disease patient. In one embodiment, the acid used to precipitate proteinaceous material is perchloric acid, for example, 70% perchloric acid. In another embodiment, the thiopurine derivative used as a substrate is 6-thioguanine. In a further embodiment, the methylated purine product is detected by fluorescence, which can be combined, if desired, with high performance liquid chromatography (HPLC).

7 Claims, 2 Drawing Sheets

METHOD OF DETERMINING THIOPURINE METHYLTRANSFERASE ACTIVITY

This application is based on, and claims the benefit of, U.S. Provisional Application No. 60/205,695, filed May 19, 2000, and entitled Method of Determining Thiopurine Methyltransferase Activity, and which is incorporated herein by reference.

BACKGROUND OF THE INVENTION

1. Field of the Invention

The present invention relates generally to thiopurine drugs used for the treatment of inflammatory bowel disease, leukemia, and organ transplantation rejection, and more specifically to methods for determining thiopurine methyltransferase activity in order to individualize dosages of 6-mercaptopurine therapy.

2. Background Information

Mercaptopurine (6-MP or 6-thiopurine) and azathioprine [6-(1-methyl-4-nitro-5-imidazolylthio)purine] are cytotoxic drugs which are effective in the treatment of ulcerative colitis and Crohn's disease (Present et al., *Annals of Internal Medicine* 111:641–649 (1989)). Both are immunosuppressive agents that act as purine antagonists and thereby inhibit the synthesis of DNA, RNA and proteins (Lennard, *European Journal of Clinical Pharmacology* 43:329–339 (1992)). 6-MP was initially used for the treatment of childhood acute lymphoblastic leukemia and for post-operative treatment of organ transplantation surgery (Burchenal et al., *Blood* 8:965–999 (1953)), and its use has since been extended to rheumatoid arthritis and inflammatory bowel disease (Kirschner, *Gastroenterology* 115:813–821 (1998)).

The prodrug azathioprine (AZA) is rapidly converted to 6-mercaptopurine through non-enzymatic, nucleophilic attack by sulfhydryl-containing compounds in the circulation. 6-MP and azathioprine (AZA), which are forms of the same drug and metabolic precursors of the active components, are acted upon by at least three competing enzymatic pathways (Lennard, supra, 1992). An overview of the action of these enzymes is shown in FIG. 1. As shown in FIG. 2, several major enzyme pathways are involved. Xanthine oxidase (XO) converts 6-mercaptopurine to 6-thiouric acid. Hypoxanthine phosphoribosyl transferase (HPRT) converts 6-mercaptopurine to 6-thioinosine-5'-monophosphate, which is a precursor to 6-thioguanine nucleotides. Thiopurine methyltransferase (TPMT) catalyzes the S-methylation of 6-mercaptopurine to methylmercaptopurine (6-MMP). Thus, 6-mercaptopurine is enzymatically converted to various metabolites, including 6-thioguanine (6-TG) and 6-thioguanine nucleotides, which are the presumptive active metabolites mediating the effects of azathioprine/6-mercaptopurine drug therapy.

The interplay of the pathways described above is genetically determined and creates a highly individualized response to azathioprine/6-mercaptopurine drug therapy. The population frequency distribution of TPMT enzyme is trimodal, with the majority of individuals (89%) having high activity, 11% having intermediate activity and about 1 in 300 (0.33%) having undetectable activity (Weinshilboum and Sladek, *Amer. J. Human Genetics* 32:651–662 (1980)). Such a trimodal relationship has been confirmed by direct measurements of TPMT enzyme activity by the Kröplin HPLC assay method (Kroplin et al., *Eur. J. Clin. Pharmacol.*, 54 265–271 (1998)). In contrast to variation in TPMT activity, there is very little inter-individual variation in XO activity and only limited data on HPRT activity (Lennard, *Eur. J. Clin. Pharm.*, 43:329–339 (1992)).

Available evidence indicates that TPMT activity effectively modulates the concentration of 6-thioguanine by shunting 6-mercaptopurine into the production of 6-methylmercaptopurine. Patients who less efficiently methylate these thiopurines have more extensive conversion to 6-thioguanine nucleotides, which can lead to potentially fatal hematopoietic toxicity. Thus, patients with intermediate or low TPMT activity can be more susceptible to toxic side effects of azathioprine/6-mercaptopurine therapy (Present et al., *Annals of Internal Medicine* 111:641–649 (1989)). Such toxic side effects include allergic reactions, neoplasia, opportunistic infections, hepatitis, bone marrow suppression, and pancreatitis; in about 1 out of 300 patients, this therapy cannot be tolerated. As a consequence, many physicians are reluctant to treat patients with azathioprine/6-mercaptopurine therapy, particularly due to the risk of infection and neoplasia.

Thus, there is a need for a method of optimizing the dose of 6-mercaptopurine by determining the level of thiopurine methyltransferase activity in a patient. Such a method would be valuable for optimizing therapeutic efficacy of azathioprine/6-mercaptopurine therapy while minimizing undesirable side effects. The present method satisfies this need and provides related advantages as well.

SUMMARY OF THE INVENTION

The present invention provides a method of determining thiopurine methyltransferase (TPMT) activity in a subject. The method includes the steps of reacting sample obtained from the subject with a thiopurine derivative that is not 6-mercaptopurine to produce a methylated purine product; contacting the reacted sample with acid, thereby precipitating proteinaceous material from the reacted sample; separating supernatant from the precipitated proteinaceous material; and detecting in the supernatant the methylated purine product, where the amount of the methylated purine product indicates a level of thiopurine methyltransferase activity in the subject. In a method of the invention, the subject can be, for example, an inflammatory bowel disease patient. In one embodiment, the acid used to precipitate proteinaceous material is perchloric acid, for example, 70% perchloric acid. In another embodiment, the thiopurine derivative used as a substrate is 6-thioguanine. In a further embodiment, the methylated purine product is detected by fluorescence, which can be combined, if desired, with high performance liquid chromatography (HPLC).

DETAILED DESCRIPTION OF THE INVENTION

Figure 1:
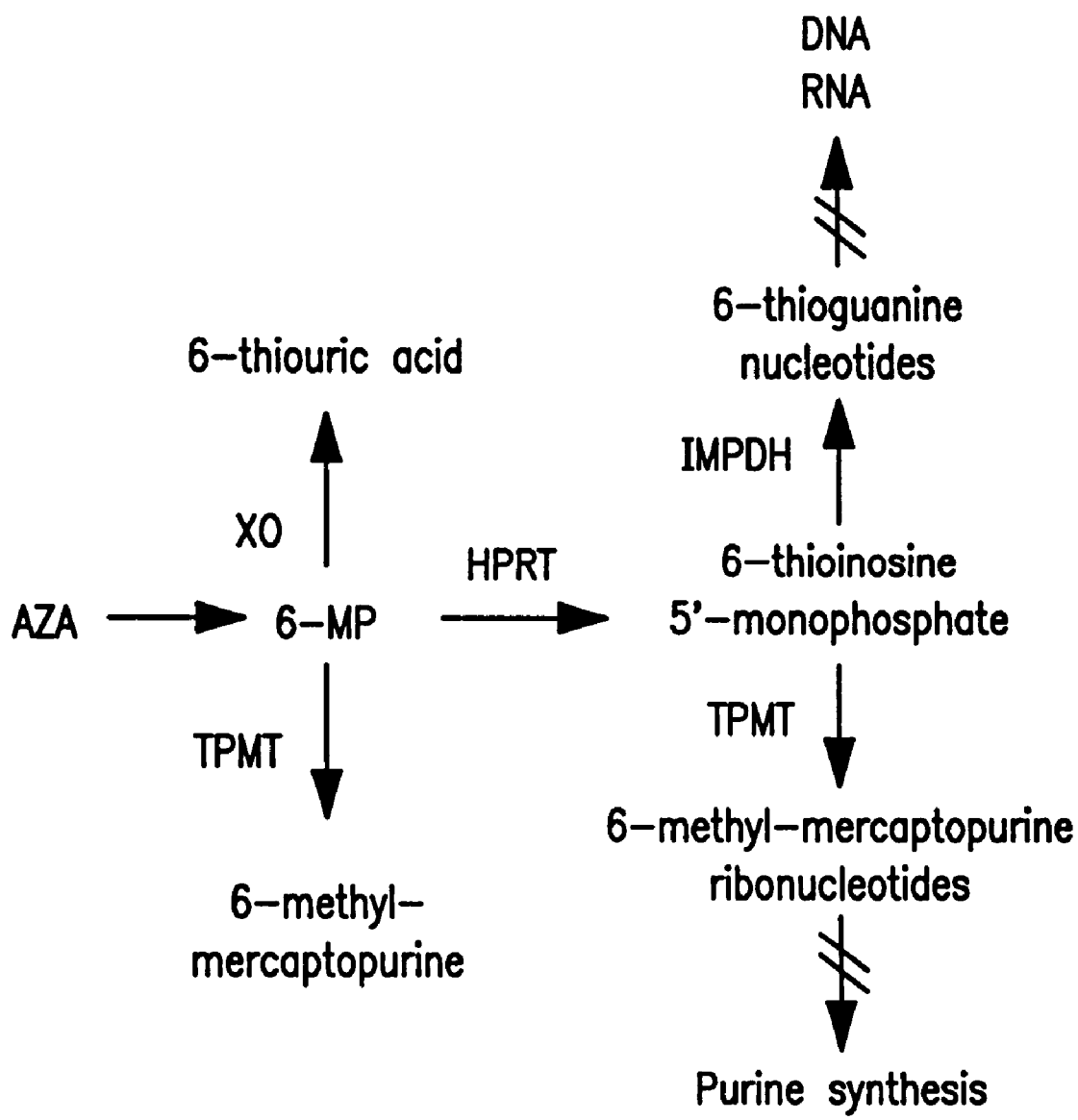
FIG. 1 shows a general schematic of the metabolism of azathioprine and 6-mercaptopurine. Oral azathioprine is rapidly converted to 6-mercaptopurine by a nonenzymatic process. Initial 6-MP transformations occur along competing catabolic (XO, xanthine oxidase; TPMT) and anabolic (HPRT, hypoxanthine phosphoribosyltransferase) enzymatic pathways. Once formed by HPRT, 6-TIMP may be transformed into 6-TGN by the rate-limiting enzyme inosine monophosphate dehydrogenase (IMPDH) or methylated into 6-MMPR (Dubinsky et al., *Gastroenterology* 118:705–713 (2000)).
Figure 2:
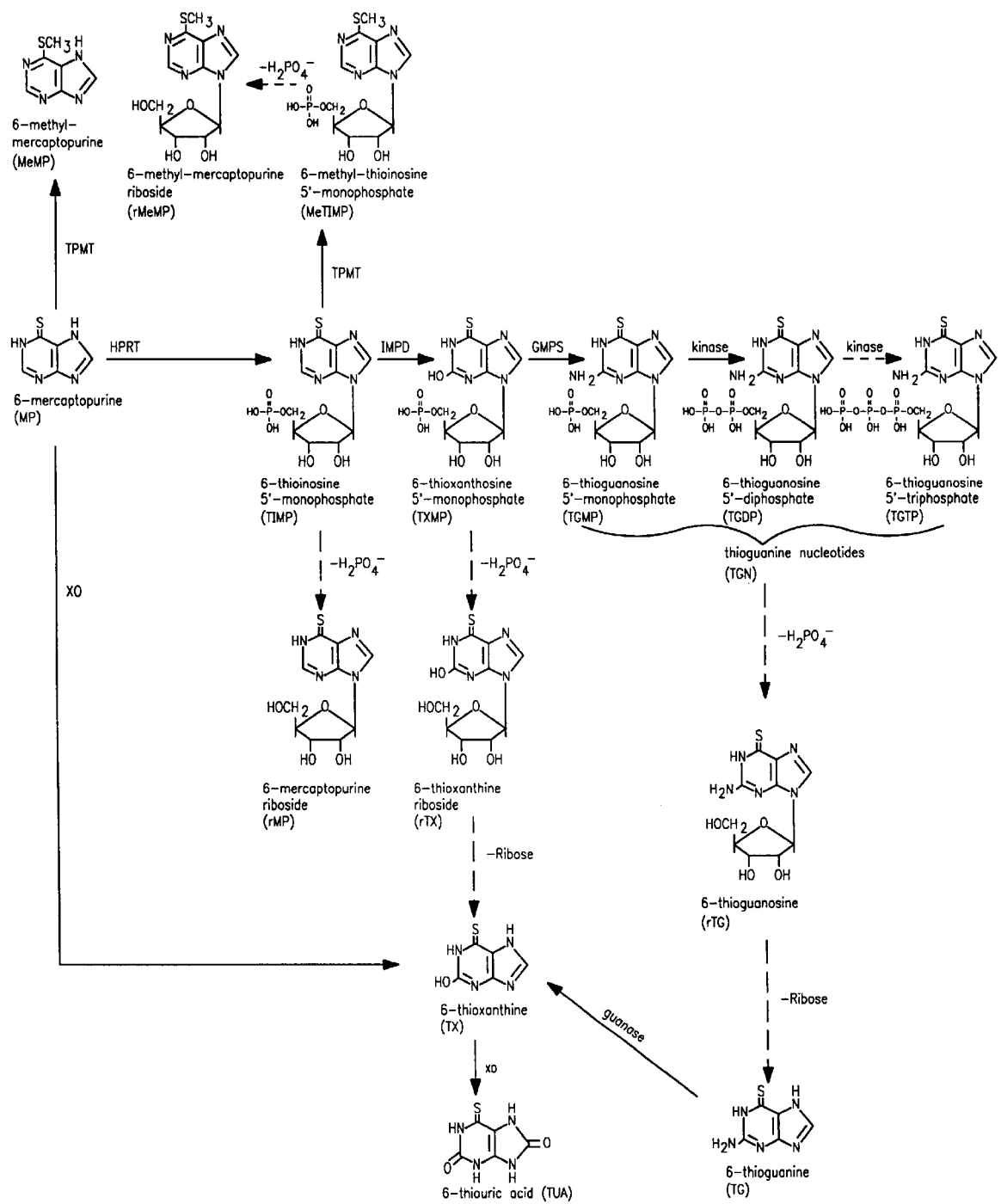
FIG. 2 shows the metabolism of azathioprine and 6-mercaptopurine. 6-mercaptopurine metabolic pathways are indicated by solid arrows; dashed arrows indicate putative products of dephosphorylation to nucleotides and further catabolism to nucleobases. HPRT, hypoxanthine phosphoribosyltransferase; TMPT, thiopurine methyltransferase; XO, xanthine oxidase; IMPD, inosine monophosphate dehydrogenase; GMPS, guanosine monophosphate synthetase.

Effective treatment of inflammatory bowel diseases such as Crohn's disease and ulcerative colitis with 6-mercaptopurine and the related pro-drug, azathioprine (AZA), is complicated by the toxic side effects of this therapy in patients with low or intermediate TPMT enzyme activity. Such toxic side effects include allergic reactions, neoplasia, opportunistic infections, hepatitis, bone marrow suppression, and pancreatitis. Therefore, it is critical that TPMT activity be measured in candidates for 6-mercaptopurine treatment in order to administer the appropriate dose to patients with intermediate levels of activity and to avoid therapy in patients with extremely low TMPT activity. Additionally, TPMT activity can be assayed in patients who have begun azathioprine/6-mercaptopurine therapy in order to ensure that appropriate enzyme levels are present for the dose of drug administered.

The present invention is directed to the discovery of a rapid and reliable method for determining thiopurine methyltransferase (TPMT) activity in a subject and is particularly advantageous in that enzyme activity can be determined even if the patient has already been medicated with 6-mercaptopurine or azathioprine. A method of the invention for determining TPMT activity in a subject includes the steps of reacting sample obtained from the subject with a thiopurine derivative that is not 6-mercaptopurine to produce a methylated purine product; contacting the reacted sample with acid, thereby precipitating proteinaceous material from the reacted sample; separating supernatant from the precipitated proteinaceous material; and detecting in the supernatant the methylated purine product, where the amount of the methylated purine product indicates a level of thiopurine methyltransferase activity in the subject. In a method of the invention, the subject can be, for example, an inflammatory bowel disease patient. In one embodiment, the acid used to precipitate proteinaceous material is perchloric acid, for example, 70% perchloric acid. In another embodiment, the thiopurine derivative used as a substrate is 6-thioguanine. In a further embodiment, the methylated purine product is detected by fluorescence, which can be combined, if desired, with high performance liquid chromatography (HPLC).

Thus, the present invention is directed to a method for quantitatively measuring and monitoring the activity of TPMT in human peripheral blood. As disclosed in Example I, direct enzymatic turnover of a thiopurine (6-thioguanine) yielded the fluorescent product 6-methylthioguanine. The level of the specific 6-methylthioguanine product resulting from the enzyme turnover was separated from other assay components by perchloric acid precipitation, followed by high performance liquid chromatography (HPLC) and quantitative detection by a high sensitivity fluorometric detector. This novel assay method allows determination of TPMT enzyme activity even if the patient is taking 6-MP or AZA therapy and streamlines the sample extraction for rapid quantitation.

Using this procedure, patients were readily separated into three groups: those who were genetically wild type had enzyme levels of greater than 23.60 nmoles 6-mTGN/g Hb/hr; those heterozygous for one of three previously characterized TPMT mutations had TMPT activity levels from 6.76 to 23.6 nmoles 6-mTGN/g Hb/hour; and an individual homozygous low at the TPMT locus had a TPMT activity level less than 6.76 6-mTGN/g Hb/hour (1.1 6-mTGN/g Hb/hour). Thus, the level of fluorescent methylated 6-thioguanine product (6-mTG) was correlated with TMPT activity and can be used to prevent toxic side effects in patients with low or intermediate TPMT activity levels.

The methods of the invention are particularly useful for treating IBD, or subtypes of IBD, which has been classified into the broad categories of Crohn's disease and ulcerative colitis. Crohn's disease (regional enteritis) is a disease of chronic inflammation that can involve any part of the gastrointestinal tract. Commonly, the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity. The most frequent symptoms of Crohn's disease are abdominal pain, diarrhea and recurrent fever, and this disease also can be associated with intestinal obstruction or fistula, which is an abnormal passage between diseased loops of bowel. Crohn's disease further can be associated with complications such as inflammation of the eye, joints and skin; liver disease; kidney stones or amyloidosis.

The pathology of Crohn's disease includes transmural inflammation, involving all layers of the bowel wall. Thickening and edema, for example, typically appear throughout the bowel wall, with fibrosis also present in long-standing disease. Furthermore, the inflammation characteristic of Crohn's disease also is discontinuous in that segments of inflamed tissue, known as "skip lesions," are separated by apparently normal intestine. Linear ulcerations, edema, and inflammation of the intervening tissue lead to a "cobblestone" appearance of the intestinal mucosa, which is distinctive of CD. A hallmark of Crohn's disease is the presence of discrete aggregations of inflammatory cells, known as granulomas, which are generally found in the submucosa (Rubin and Farber, *Pathology* (Second Edition) Philadelphia: J. B. Lippincott Company (1994)).

The inflammatory bowel disease ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with ulcerative colitis. Local and systemic complications of UC include arthritis, eye inflammation such as uveitis, skin ulcers and liver disease. In addition, ulcerative colitis, and especially long-standing, extensive disease, is associated with an increased risk of colon carcinoma.

Ulcerative colitis generally is a diffuse disease that usually extends from the most distal part of the rectum for a variable distance proximally. Sparing of the rectum or involvement of the right side (proximal portion) of the colon alone is unusual in ulcerative colitis. The inflammatory process of ulcerative colitis is limited to the colon and is distinguished by a superficial inflammation of the mucosa that generally spares the deeper layers of the bowel wall. (Rubin and Farber, supra, 1994).

The methods of the invention are useful for determining TPMT activity in a variety of subjects, including patients having inflammatory bowel disease or leukemia, and organ or allograft transplant recipient. As used herein, the term "subject" means any animal which expresses the enzyme thiopurine methyltransferase, including a human, non-human primate, rabbit, rat or mouse, and especially a human. A subject can be a patient having an inflammatory bowel disease (ulcerative colitis or Crohn's disease); leukemia; or a transplant recipient. A subject may or may not have been treated with 6-mercaptopurine or azathioprine therapy.

As used herein, the term "sample" refers to biological material obtained from a subject and encompasses any material that contains the cytoplasmic enzyme thiopurine methyltransferase. A sample can be, for example, whole blood, plasma, saliva or other bodily fluid or tissue that contains cells. A preferred sample is whole blood, from which red blood cells can be obtained as described in Example I.

The methods of the invention involve reacting a sample with a thiopurine derivative that is not 6-mercaptopurine. As used herein, the term "thiopurine derivative" refers to a thioxopurine, thiopurine or a derivative or analog thereof which acts as a methyl acceptor when acted upon by thiopurine methyltransferase. A thiopurine derivative useful in the invention can be a naturally occurring or non-naturally occurring substrate for thiopurine methyltransferase which has a structure similar to a thiopurine or thioxopurine, for example, 6-thioguanine, and can occur in reduced or oxidized form. Additional thiopurine derivatives are known in the art and include thioinosine, thioadenine, thioguanosine and thioadenosine. It should be understood that any thiopurine derivative other than 6-mercaptopurine can be useful in the methods of the invention. Such a thiopurine derivative has the following structure

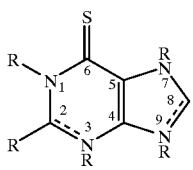

and is a fused 6.5 membered ring derivative with a thioxo or thio at the 6 position of the 6-membered ring, ring nitrogens at the 1 and 3 positions of the 6-membered ring and ring nitrogens at the 7 and 9 positions of the 5-membered ring. For example, where R at the 2-position of the 6-membered ring is amino, the thiopurine derivative is thioguanine. It is understood that the R groups at the 1, 2, 3, and 7, 8, and 9 positions are independent and can be, for example, a sugar, halide, $C_1$–$C_6$ alkyl, OH, amino, mono or di-substituted amino (where substitutions are $C_1$–$C_6$ alkyl or substituted alkyl) or substituted $C_1$–$C_6$ alkyl (where substitutions are one or more OH, halide, amino or mono or disubstituted amino), provided that the R group does not inhibit thiopurine methyltransferase activity.

In one embodiment, a thiopurine derivative useful in the invention is a compound which fluoresces when methylated. For example, 6-thioguanine is methylated by thiopurine methyltransferase to the fluorescent product 6-methyl thioguanine. The skilled person understands that these and other non-6-MP substrates for thiopurine methyltransferase can be thiopurine derivatives useful in the invention.

As used herein, the term "methylated purine product" refers to the chemical product generated as a result of thiopurine methyltransferase activity upon a thiopurine derivative. Methylated purine products include 6-methylthioguanine, and analogs thereof, which are produced by methylation of 6-thioguanine.

In a method of the invention, proteinaceous material is precipitated away from the methylated purine product. As used herein, the term "acid" refers to a reagent that is capable of effecting preferential precipitation of proteinaceous material from solution, while methylated purine products such as 6-methylthioguanine are not precipitated. One skilled in the art understands that an acid useful in the invention does not substantially destroy, degrade or otherwise affect detection of methylated purine product. Exemplary acids useful in the invention are disclosed herein as perchloric acid; sulfuric acid, phosphoric acid and glacial acetic acid (see Example III). Additional acids useful in the invention can be identified by the ability to yield a substantially similar TPMT activity level for a particular sample, as compared to a sample contacted with 70% perchloric acid.

As used herein, the term "detecting" refers to a process by which the amount of methylated purine product is determined. Methylated purine products, such as 6-mTG, can be detected by a variety of quantitative techniques suitable for distinguishing methylated purine products from thiopurine derivatives and other compounds. Methylated purine products can be conveniently detected, for example, using high performance liquid chromatography (HPLC). Additional methods for detecting methylated purine products include capillary electrophoresis, gas chromatography (GC), gas chromatography-mass spectroscopy (GC-MS) and thin layer chromatography (TLC). The skilled person understands that these and other methods for quantitating the amount of methylated purine product can be useful in the invention.

The following examples are intended to illustrate but not limit the present invention.

EXAMPLE I

Quantitative Determination of Thiopurine Methyltransferase Enzyme Activity Levels in Human Red Blood Cells This example describes quantitative determination of thiopurine methyltransferase (TPMT) activity using 6-thioguanine as a substrate.

A. Blood Sample Preparation

Whole blood samples were washed in normal saline, and the hemoglobin count determined prior to freezing. Briefly, blood samples were collected in ethylene diamine tetraacetic acid (EDTA), and the EDTA-treated whole blood centrifuged for 3 minutes at 3500 rpm at 10° C. in a tabletop centrifuge (Beckman, Fullerton, Calif.; Model #TJ-6R). Plasma was examined for hemolysis, and sample was rejected if hemolysis was detected. After removing the plasma, packed cells were washed one time with an equal volume of 0.9% saline and centrifuged as described above. A hemoglobin count was determined using a Coulter ONYX cell counter. After counting, the washed packed red blood cells (RBCs) were diluted 1:5 with 0.02 M phosphate buffer (pH 7.4) and stored at −70° C. until analysis.

B. Enzymatic Reaction and Protein Precipitation

Red blood cell lysates were incubated with 6-thioguanine, and proteinaceous material subsequently precipitated with perchloric acid as described below.

"Unknown" refers to an enzymatic reaction performed with a patient sample. "Baseline" refers to an enzymatic reaction performed with a patient sample without the methyl donor, S-adenosyl methionine (SAM). "Blank" refers to an enzymatic reaction performed with normal pooled cells without SAM. "Control" refers to an enzymatic reaction performed with lysate having a previously determined "low" activity, "medium" activity, or "high" activity. Calibration standards refer to a 6-methylthioguanine standard containing lysate but not SAM.

The following components were combined: 150 μL 3 mM 6-thioguanine in 0.1 M Phosphate Buffer, pH 7.4 (Sigma Chemical, Catalog # A-4882); 50 μL distilled H$_2$O for a "blank" or "baseline" sample or 0.16 mM SAM Solution (Sigma Chemical, St. Louis, Mo.; Catalog # A-7007) for an "unknown" sample; 50 µl thawed red blood cell lysate (patient cell lysate for "unknown" or "baseline", normal pooled cell lysate for calibration standard and "blank" sample, control cell lysate for "control" sample); and 50 µl of 6-methylthioguanine standard for calibration standard sample.

Mixtures were incubated in a 37° C. shaking water bath for 1 hour and subsequently cooled on ice for 5 to 60 minutes. A volume of 50 µL 70% perchloric acid (Fisher, Pittsburgh, Pa.; Catalog # MK2766-500) was added to a final concentration of 11.67%, and the acidified sample centrifuged for 5 minutes to precipitate proteinaceous material. Supernatant (280 µL) was transferred to an HPLC autosampler vial (Hewlett-Packard, Palo Alto, Calif.; catalog # 5183–4504) fitted with an insert (Hewlett-Packard, catalog # 5181–3377).

C. HPLC Detection of 6-methylthioguanine

HPLC with fluorescent detection was performed to measure the concentration of 6-methylthioguanine in patient samples essentially as follows.

A Hewlett Packard HPLC System (Model # 1100) with in-line fluorometer (Series 1100) was used for analysis. A C18 reverse phase column (Waters, Milford, Mass.; Part # 186000494) with an in-line filter (Hewlett-Packard, Catalog # 01090–68072) was equilibrated in freshly prepared mobile phase (0.1 M $H_3PO_4$, 1 mM DTT in distilled $H_2O$/acetonitrile, 95/5%, v/v). A primer solution injection was included in addition to calibration standards, controls and patient samples, and matrix blanks were run immediately before and after the study or control samples.

Each sample (100 µL) was injected onto the column with a flow rate of 1.2 mL/min and run under isocratic conditions. Fluorescence was monitored by setting the excitation wavelength to 315 nm and the emission wavelength to 390 nm. The retention time for 6-methylthioguanine was 5.2 minutes ±20%.

D. Determination of TPMT Activity

Enzyme activity was expressed as nmol 6-methylthioguanine/gram hemoglobin in 50 µL of lysate/hour. Patient samples that had less than 6.76 nmoles 6-methylthioguanine/g Hb/hour indicate a subject possessing low TPMT activity. Patient samples having 6.76 to 23.60 nmoles 6-methylthioguanine/g Hb/hour indicate a subject possessing intermediate (heterozygous) TPMT activity. Patient samples having greater than 23.60 nmoles 6-methylthioguanine/g Hb/hour indicate a subject possessing high (wild type) TPMT activity.

EXAMPLE II

Correlation of TPMT Activity with TPMT Genotype

This example demonstrates that the methods of the invention for determining TPMT activity produce results that correlate with TPMT genotyping.

Previous studies of various ethnic populations have shown that roughly 89% of individuals express wild type (high) TPMT activity, while about 11% express intermediate activity and less than 1% (approximately 0.3%) express very low or undetectable TPMT activity. TPMT activity levels assayed using perchloric acid precipitation followed by HPLC and fluorescence detection as described in Example I were correlated to several TPMT genotype classes: TPMT*2-G238C in exon 5; TPMT*3A-G460A in exon 7, and TPMT*3-A719G in exon 10. To a large degree, these three mutations determine TPMT enzyme activity levels in humans.

TPMT enzyme units and TPMT genotypes were measured for 44 individuals with a wild type genotype, 6 heterozygous individuals, and 1 homozygote low individual, with red cell lysates coded and assayed in duplicate. The corresponding DNA was also coded and genotype was determined by ProPredictR$_x$ TPMT Genetic Analysis at Prometheus Laboratories (San Diego, Calif.). Briefly, genotypes were determined by isolation and purification of DNA from whole blood, following by amplification of regions of interest by the polymerase chain reaction in the presence of fluorescent-labeled primers. The three amplified regions on chromosome 6 were the following: TPMT*2-G238C in exon 5, TPMT*3A-G460A in exon 7, and TPMT*3-A719G in exon 10. Subsequently, the labeled PCR products were digested with specific restriction enzymes, and the digested and labeled PCR fragment products analyzed on an ABI Prism 310 Genetic Analyzer using capillary electrophoresis. The mean, standard deviation, range of results, and 95% confidence interval were calculated for each genotype group. ANOVA was performed on the three genotype groups to determine the p values (significance) of the means between the groups.

The results of this analysis demonstrated that there was very good discrimination of homozygote low patients as compared to heterozygote and wild type patients (see Table 1). The distinction between the patient which was homozygous low for TPMT agreed with a published report in which all homozygote low patients had TPMT values below 2 nmoles 6-mTGN/gm Hb/hour. The heterozygote group had TPMT values ranging from a low of 9.7 to a high of 19.8 nmoles 6-mTGN/gm Hb/hour, agreeing well with a published report in which heterozygotes had TPMT activities ranging from a low of about 10 to an assigned high value of 23.5 nmoles 6-mTGN/gm Hb/hour. One wild type TPMT activity level (19.6) overlapped with the heterozygote range of 9.7–19.8 nmoles 6-mTGN/gm Hb/hour. This particular patient was also measured by the Mayo Clinic radiochemical assay and has been shown to have a somewhat low wild type phenotype (Mayo reported a value of 16.7 U/ml RBC as compared to their normal range of 13.8–25.1 U/ml RBC).

The difference in mean TPMT activity between the homozygote low and heterozygote populations [$X_{L-L}$=1.1 versus $X_{H-L}$=15.18] shows that homozygote low individuals can be reliably distinguished from those heterozygous for wild type TMPT and from those who are homozygous wild type at the three TPMT polymorphic sites assayed (see Table 1). Furthermore, the unpaired t test indicates that the wild type and heterozygote populations were significantly different ($p<0.0001$, two-tailed). Due to the small sample size in the homozygote low group, which represents a rare genotype, a similar analysis could not be performed between the wild type and homozygote low or heterozygote and homozygote low groups.

TABLE 1

Results of Genotyping versus Phenotyping Correlation for TPMT

| Parameter: | Wild Type | Wild Type | Hetero-zygote | Hetero-zygote | Homo-zygote Low | Homo-zygote Low |
|---|---|---|---|---|---|---|
| Study: | This Study | Kröplin | This Study | Kröplin | This Study | Kröplin |
| Count in Group | 44 | 183 | 6 | 31 | 1 | 5 |
| Average | 35.87 | Not | 15.18 | Not | 1.1 | Not |

TABLE 1-continued

Results of Genotyping versus
Phenotyping Correlation for TPMT

| Parameter: | Wild Type | Wild Type | Hetero-zygote | Hetero-zygote | Homo-zygote Low | Homo-zygote Low |
|---|---|---|---|---|---|---|
| HPLC Result | given | | given | | given | |
| Standard Deviation | 8.541 | — | 4.210 | — | N/A | — |
| Median Value | 35.30 | 40.7 | 15.550 | 15.6 | 1.1 | <2 |
| Lowest Value in Group | 19.60 | — | 9.70 | — | 1.1 | — |
| Highest Value in Group | 63.7 | 67 | 19.8 | — | 1.1 | — |

The recommendations for setting cut-off values for the three genotype categories are shown in Table 2:

TABLE 2

| Genotype | Cut-off Range (nmoles 6-mTGN/g Hb/hr) | Clinical Relevance |
|---|---|---|
| Homozygote low | <6.76 | Patient should not receive 6-MP or Azathioprine due to risk of cytotoxicity by 6-TGN. |
| Heterozygote | 6.76–23.60 | Patient will safely tolerate low initial doses of 6-MP or AZA. Increasing doses should be accompanied by close monitor of metabolites. |
| Wild type | >23.60 | Patient will safely tolerate standard initial doses of 6-MP or AZA. Increasing doses should be accompanied by close monitoring of metabolites |

Cut-offs for the trimodal distribution determined for TPMT levels assayed using perchloric acid precipitation and HPLC/fluorescence detection are shown in comparison to the cut-offs for homozygote low, heterozygote and wild type genotypes recommended based on the Mayo Clinic radiochemical method. These two methods rely on different TPMT substrates, which may result in different enzyme kinetics and different enzyme turnover rates. Both methods resulted in a trimodal distribution TPMT activity. Table 3 provides a correlation of the recommended ranges for both methods:

TABLE 3

| Genotype | Prometheus (6-mTGN/g Hb/hr) | Mayo (U/ml RBC) |
|---|---|---|
| Homozygote low | <6.76 nmoles | <5.0 |
| Heterozygote | 6.76–23.60 nmoles | 5.0–13.7 |
| Wild type | >23.60 nmoles | 13.8–25.1 |

EXAMPLE III

Survey of Acids for Protein Precipitation

This example describes the use of several different acids for the precipitation of proteinaceous material from samples containing 6-methylthioguanine.

A calibration standard curve and high controls were prepared as described in Example I. Both the standard curve and controls contained 6-methyl thioguanine (6-mTG), the product of the reaction catalyzed by TPMT, making the reaction portion of the protocol unnecessary. To the standard curve and one set of tubes, 11 M perchloric acid (PCA) was added. In place of the perchloric acid, one of the following acids was added to each set of samples: 17 M acetic acid (glacial) to a final concentration of 2.83 M; 16 M nitric acid ($HNO_3$) to a final concentration of 2.67 M; 15 M phosphoric acid ($H_3PO_4$) to a final concentration of 2.5 M; 18 M sulfuric acid ($H_2SO_4$) to a final concentration of 3 M, or 6 M trichloroacetic acid (TCA) to a final concentration of 1 M. Samples were then processed and analyzed as described in Example I.

As shown in Table 4, sulfuric acid, phosphoric acid and acetic acid treatment of RBC lysate yielded TPMT activity determinations similar to those obtained after perchloric acid precipitation. However, 6-methylthioguanine was undetectable in lysates following treatment with trichloroacetic acid or nitric acid. These results indicate that sulfuric acid, phosphoric acid or glacial acetic acid can be used in place of perchloric acid to preferentially precipitate proteinaceous material from lysates without degrading a methylated purine product such as 6-mTG in the supernatant.

TABLE 4

| Acid | Mean TPMT activity (nmol 6-mTG/gm Hb) | Standard Deviation | Percent coefficient of Variation |
|---|---|---|---|
| PCA | 62.829 | 0.63 | 1.01% |
| $H_2SO_4$ | 58.896 | 1.12 | 1.91% |
| $H_3PO_4$ | 58.937 | 0.42 | 0.71% |
| Acetic | 62.230 | 1.60 | 2.57% |
| TCA | 0.000 | 0.00 | NA |
| $HNO_3$ | 0.000 | 0.00 | NA |

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of determining thiopurine methyltransferase (TPMT) activity in a subject, comprising the steps of:

(a) reacting sample obtained from said subject with a thiopurine derivative to produce a methylated purine product, provided that said thiopurine derivative is not 6-mercaptopurine;

(b) contacting said reacted sample with acid, thereby precipitating proteinaceous material from said reacted sample;

(c) separating supernatant from said precipitated proteinaceous material; and (d) detecting in said supernatant said methylated purine product, wherein the amount of said methylated purine product indicates a level of thiopurine methyltransferase activity in said subject.

2. The method of claim 1, wherein said subject is an inflammatory bowel disease patient.

3. The method of claim 1, wherein said acid is perchloric acid.

4. The method of claim 3, wherein said perchloric acid is 70% perchloric acid.

5. The method of claim 1, wherein said thiopurine derivative is 6-thioguanine.

6. The method of claim 5, wherein said methylated purine product is detected by fluorescence.

7. The method of claim 1, wherein said methylated purine product is detected by high performance liquid chromatography (HPLC).

* * * * *

UNITED STATES PATENT AND TRADEMARK OFFICE
CERTIFICATE OF CORRECTION

PATENT NO. : 6,576,438 B2
DATED : June 10, 2003
INVENTOR(S) : Barstad

It is certified that error appears in the above-identified patent and that said Letters Patent is hereby corrected as shown below:

Title page,
Item [56], References Cited, OTHER PUBLICATIONS, add the following:
-- Sandborn and Tremaine, "Measurement of thiopurine methyltransperase (TMPT) activity in patients with inflammatory bowel disease (IBD) does not predict side effects from treatment with 6-mercaptopurine (6-MP) or azathioprine," Mayo Clin. Proc., 67:981-990 (1992)

Stupans et al., "Human thiopurine methyltransferase: no evidence of activation by its substrates, Life Sci., 62:343-350 (1998)

Su et al., "Assay of 6-mercaptopurine and its metabolites in patient plasma by high-performance liquid chromatography with diode-array detection," J. Chromatograpy B., 732:459-468 (1999)

Weinshilboum and Sladek, "Mercaptopurine pharmacogenetics: monogenic inheritance of erythrocyte thiopurine methyltransferase activity," Am. J. Hum. Genet., 32:651-662 (1980)

Weinshilboum et al., "Human erythrocyte thiopurine methyltransferase: radiochemical microassay and biochemical properties," Clinica Chimica Acta, 85:323-335 (1978) --.

Signed and Sealed this

Eleventh Day of April, 2006

JON W. DUDAS
*Director of the United States Patent and Trademark Office*